United States Patent
Reinitz

(10) Patent No.: US 7,316,694 B2
(45) Date of Patent: Jan. 8, 2008

(54) SURGICAL SUTURING APPARATUS

(76) Inventor: Karl Reinitz, 75 Sheridan Rd., Arnold, MD (US) 21012

( * ) Notice: Subject to any disclaimer, the term of this patent is extended or adjusted under 35 U.S.C. 154(b) by 471 days.

(21) Appl. No.: 10/721,691

(22) Filed: Nov. 26, 2003

(65) Prior Publication Data

US 2005/0113848 A1    May 26, 2005

(51) Int. Cl.
*A61B 17/04* (2006.01)
*A61B 17/06* (2006.01)
(52) U.S. Cl. .................. 606/144; 606/139; 606/222; 606/224
(58) Field of Classification Search .............. 606/144, 606/139, 145–150, 181, 188, 222–227, 167, 606/138; 112/169, 80.03; 24/706.2–706.9, 24/66.8, 67 R; 604/164.08
See application file for complete search history.

(56) References Cited

U.S. PATENT DOCUMENTS

| | | | | |
|---|---|---|---|---|
| 2,692,415 A | * | 10/1954 | Forde | .......... 24/709.4 |
| 5,151,089 A | * | 9/1992 | Kirk et al. | .......... 604/192 |
| 5,273,053 A | | 12/1993 | Pohndorf | |
| 5,336,239 A | * | 8/1994 | Gimpelson | .......... 606/223 |
| 5,374,275 A | | 12/1994 | Bradley et al. | |
| 5,403,328 A | | 4/1995 | Shallman | |
| 5,431,666 A | | 7/1995 | Sauer et al. | |
| 5,437,680 A | | 8/1995 | Yoon | |
| 5,468,251 A | * | 11/1995 | Buelna | .......... 606/223 |
| 5,613,975 A | | 3/1997 | Christy | |
| 5,628,757 A | * | 5/1997 | Hasson | .......... 606/148 |
| 5,632,752 A | | 5/1997 | Buelna | |
| 5,662,663 A | | 9/1997 | Shallman | |
| 5,665,096 A | * | 9/1997 | Yoon | .......... 606/139 |
| 5,690,652 A | | 11/1997 | Wurster et al. | |
| 5,776,148 A | | 7/1998 | Christy | |
| 5,824,009 A | | 10/1998 | Fukuda et al. | |
| 5,827,291 A | | 10/1998 | Fucci et al. | |
| 5,830,125 A | | 11/1998 | Scribner et al. | |
| 5,830,220 A | | 11/1998 | Wan et al. | |
| 5,876,412 A | | 3/1999 | Piraka | |
| 5,904,692 A | | 5/1999 | Steckel et al. | |
| 5,908,426 A | | 6/1999 | Pierce | |
| 5,919,199 A | | 7/1999 | Mers Kelly et al. | |
| 5,948,001 A | | 9/1999 | Larsen | |
| 5,964,773 A | * | 10/1999 | Greenstein | .......... 606/148 |

(Continued)

OTHER PUBLICATIONS

Author Unknown, "Inlet CloSure Procedure Kit," sales brochure for Inlet Medical Inc., publication date unknown.

(Continued)

*Primary Examiner*—Todd E. Manahan
*Assistant Examiner*—Amy T. Lang

(57) ABSTRACT

A surgical suturing device has a body with a "J"-shaped suturing needle attached. One end of a movable arm is pivotably attached to the body so that the other end of the movable arm may swing into and out of engagement with the tip of the suturing needle. The movable arm is engaged by a rod that slides transversely within the body. The moveable arm swings in response to pressure on a thumb nut that moves the rod. Rod movement is resisted by a compression spring within the body. The device allows a surgeon to suture the fascial layer from within a surgical incision. The surgeon avoids unwanted penetration of tissue by pressing the thumb nut to cause the movable arm to engage and cover at least a portion of the needle tip.

14 Claims, 5 Drawing Sheets

U.S. PATENT DOCUMENTS

| | | |
|---|---|---|
| 6,059,800 A | 5/2000 | Hart et al. |
| 6,077,278 A | 6/2000 | Mayer |
| 6,110,183 A | 8/2000 | Cope |
| 6,113,610 A | 9/2000 | Poncet |
| 6,152,936 A | 11/2000 | Christy et al. |
| 6,283,979 B1 | 9/2001 | Mers Kelly et al. |
| 6,306,158 B1 | 10/2001 | Bartlett |
| 6,322,570 B1 | 11/2001 | Matsutani et al. |
| 6,332,889 B1 | 12/2001 | Sancoff et al. |
| 6,346,111 B1 | 2/2002 | Gordon et al. |
| 6,355,050 B1 | 3/2002 | Andreas et al. |
| 6,443,962 B1 | 9/2002 | Gaber |
| 7,122,040 B2 * | 10/2006 | Hill et al. .................. 606/144 |
| 2004/0236356 A1 * | 11/2004 | Rioux et al. ................ 606/144 |

OTHER PUBLICATIONS

Elashry, "Comparative Study of Pirt-Closure Techniques Following Laparoscopic Surgery," Journal of the American College of Surgeons, 1996, 183:335-344.

* cited by examiner

FIG. 4
FIG. 5
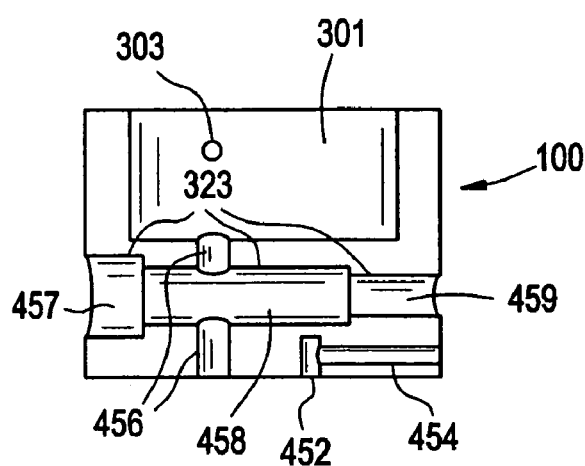
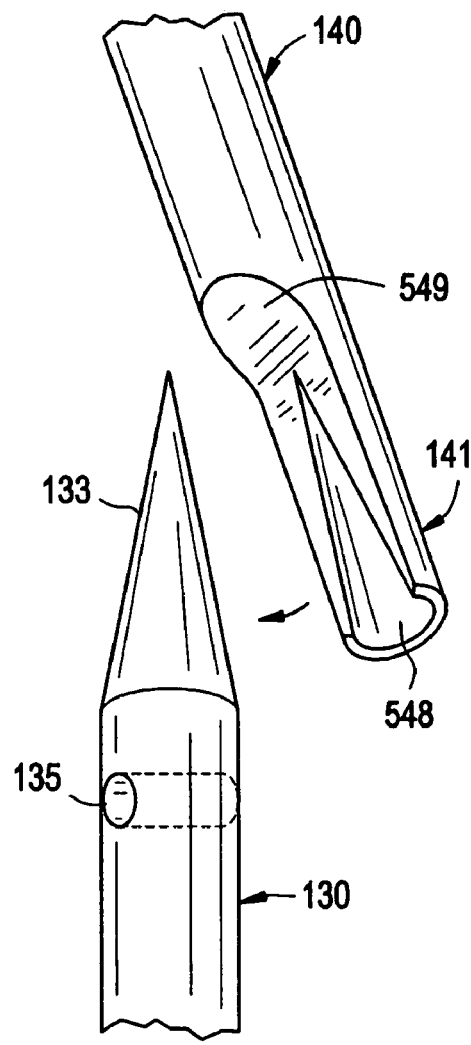

SURGICAL SUTURING APPARATUS

BACKGROUND

When suturing a surgical incision, a surgeon generally attempts to close the incision in a manner that minimizes scarring, hernias, and the likelihood of infection. A common technique is to anchor a suture on either side of an incision within the relatively tough fascial layer.

However, placing a suture through this inner tissue layer without damaging surrounding tissue and organs may be difficult under the best of circumstances and almost impossible where the patient is very obese and/or the incision is very small. A surgeon may have difficulty reaching into the incision and even more difficulty seeing the surrounding tissue beyond his fingers. Additionally, a suture needle that pierces tissue from an outer tissue layer toward the interior of the body may accidentally puncture a blood vessel or an organ.

A curved or inverted needle can provide a means for penetrating the fascial layer from beneath, thereby reducing the risk of accidental puncture. An inverted needle attached to an elongated shaft can be inserted into a small and/or deep incision without blocking the surgeon's view, simplifying the task of puncturing the fascial layer from beneath in the optimum location.

However, an inverted needle presents new difficulties once the suture is placed, since the upwardly-directed point tends to snag tissue while being withdrawn and relocated. Attempts to mitigate this problem usually involve retracting the needle into a hollow shaft or masking the tip of the needle with block of material, either by sliding the needle into the block or the block onto the needle.

In any case, both a hollow shaft of sufficient diameter to accommodate an internal mechanism and a mask large enough to cover a needle tip spaced any distance from the shaft can obstruct the surgeon's view and impair his ability to move and place the needle.

What is needed is a surgical device that provides an inverted suture needle that a surgeon can easily mask and unmask while identifying a desirable location within the body, while moving the needle to that location, while placing a suture, and while subsequently withdrawing the device entirely. The needle and supporting apparatus should minimize the bulk of any material inserted into an incision. Once the suture is placed, the device should allow the surgeon to quickly withdraw the apparatus without concern for tissue damage.

SUMMARY

A preferred embodiment of the present invention provides such a device in the form of an apparatus with a body that fits comfortably in the palm of a surgeon's hand, a "J" suture needle attached to the body, and a moveable arm attached to the body. In this preferred embodiment the moveable arm pivots about a point within the body and has a lower tip shaped to smoothly cover the point of the needle.

The needle tip is exposed when the apparatus is in an open position. To set the apparatus in a closed position, the surgeon depresses a thumb nut protruding from one side of the body of the apparatus, causing the lower end of the moveable arm to swing away from the supporting shaft of the needle and to cover the tip of the needle. In the closed position the needle tip is protected and the needle and moveable arm form an elongated "U" so that the needle may be inserted into and withdrawn from an incision without snagging tissue.

In a typical procedure, a surgeon threads a loop of suture material through a hole near the needle tip. The surgeon depresses the thumb nut on the apparatus and inserts the closed-position needle tip into an incision, placing the needle tip at a desired location. The surgeon then releases the thumb nut to expose the needle tip. After penetrating the tissue and placing the suture, the surgeon pushes the needle inward again, presses the thumb nut to cover the needle tip, and withdraws the apparatus quickly. The remaining portion of the suture is placed on the opposite side of the incision in the same manner. The smooth, narrow shafts of the needle and moveable arm minimize apparatus bulk within an incision and allow the apparatus to be inserted and withdrawn quickly and safely, speeding surgical procedures.

All of these features and advantages of the present invention, and more, are illustrated below in the drawings and detailed description that follows.

BRIEF DESCRIPTION OF THE DRAWINGS

FIG. 4 shows a cross-sectional view of the body of a preferred embodiment of the present invention.

FIG. 5 shows a perspective view of a preferred needle tip design.

DETAILED DESCRIPTION

Figure 1:
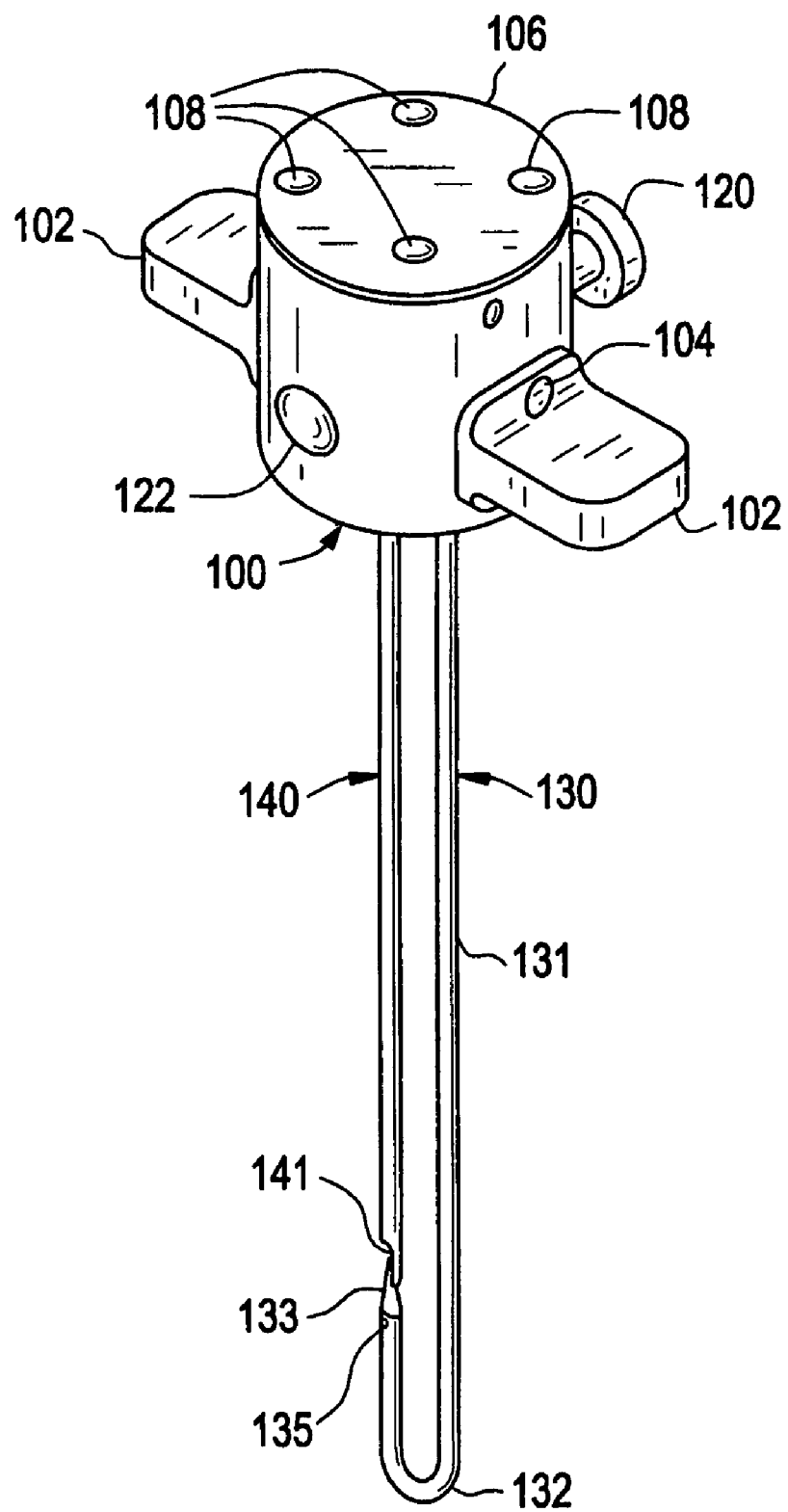
FIG. 1 shows a perspective view of a preferred embodiment of the present invention.

FIG. 1 shows a perspective view of a preferred embodiment of the present invention in a closed position. A cylindrical body 100 is machined from a block of TEFLON®. Handles 102, also TEFLON®, are screwed 104 onto opposite sides of the body 100 to provide gripping surfaces for a surgeon's fingers. A cover plate 106, also TEFLON®, may be unscrewed 108 from the top of the body 100 to provide access to the mechanism within.

A set screw 122 closes an access port to a compression mechanism chamber within the body 100. The compression mechanism reacts against a TEFLON® thumb nut 120 that is on the opposite side of the body 100 from the set screw 122 and is axially aligned with the set screw 122.

The upper end of a needle 130 is mounted within the body 100. The lower end of the needle 130 has a bend 132 that inverts the pointed tip 133 of the needle 130. The upper end of a moveable arm 140 is pivotally mounted within the body 100. When the present invention is in a closed position, the lower end of the moveable arm 140 rests against the needle tip 133 so that the needle tip 133 is at least partially covered by a tip protector 141. The tip protector 141 is a portion of the moveable arm 140 that has been machined, ground, cut, pressed, or otherwise formed to provide a recess that at least partially covers the needle tip 133.

In the elongated "U" of the preferred embodiment shown in FIG. 1, the bend 132 is a smooth radius that causes the tip 133 to be parallel to the needle shaft 131 and laterally offset from the shaft 131 a desired distance. However, in alternate embodiments the bend 132 may comprise more than one radius and/or one or more sharp angles, and the tip of 133 may angle toward, away from, or to either side of the shaft 131, with the movable arm 140 shaped and oriented correspondingly to allow the tip protector 141 to mate smoothly with tip 133. Both the needle shaft 131 and the tip protector 141 may also employ any angle, curve, or combination of angles and curves needed to allow the apparatus to reach any potential location for suture. In this embodiment the needle 130 and movable arm 140 have circular cross-sections, but any cross-sectional shape may be employed as desired. A hole 135 for suture material is bored radially through the needle a short distance below the base of the tip 133. The needle preferably comprises a proximal end and a distal end, the proximal end of the needle attached to the body and having a first central axis portion located within the proximal end of the needle, the distal end of the needle having a needle tip capable of penetrating tissue and having at least one passage to hold suture material, the tapered portion of the needle tip having a center line comprising the centroids of adjacent selected planar cross-sections of the tapered portion, each selected planar cross-section selected for having a smaller area than each proximally located planar cross-section having the same centroid as the selected planar cross-section, the distal end of the needle formed so that at least a first line is tangent to the center line and the first central axis portion.

In this preferred embodiment, the needle 130, moveable arm 140, and screws 104, 108, 122 are made of stainless steel, although other corrosion-resistant materials may be used. Other metal parts are preferentially stainless steel, and non-metal parts are preferentially TEFLON®. In alternate embodiments, non-metal parts may be plastic or ceramic. The present invention may be designed for single or repeated use. Embodiments intended for repeated use must be sterilized between uses, so materials that will tolerate sterilizing agents, solvents, or autoclave temperatures are preferred.

The body 100 described in this preferred embodiment is drilled, milled, and turned from a single block of TEFLON®, but in other embodiments the body may be assembled, cast, injection-molded, or formed by other techniques well-known in the art. The body 100, handles 102, and other parts may be contoured and/or made in other shapes without changing the nature of the invention. The handles 102 may be eliminated entirely. The relative component sizes and shapes as well as the overall size of the apparatus may vary according to surgical needs. The components and interior chambers may be resized or reconfigured to accommodate surgeons with hands of different sizes, left or right-handedness, or disabilities. For example, the component configuration in a left-handed apparatus would mirror the component configuration in a right-handed apparatus.

Figure 2:
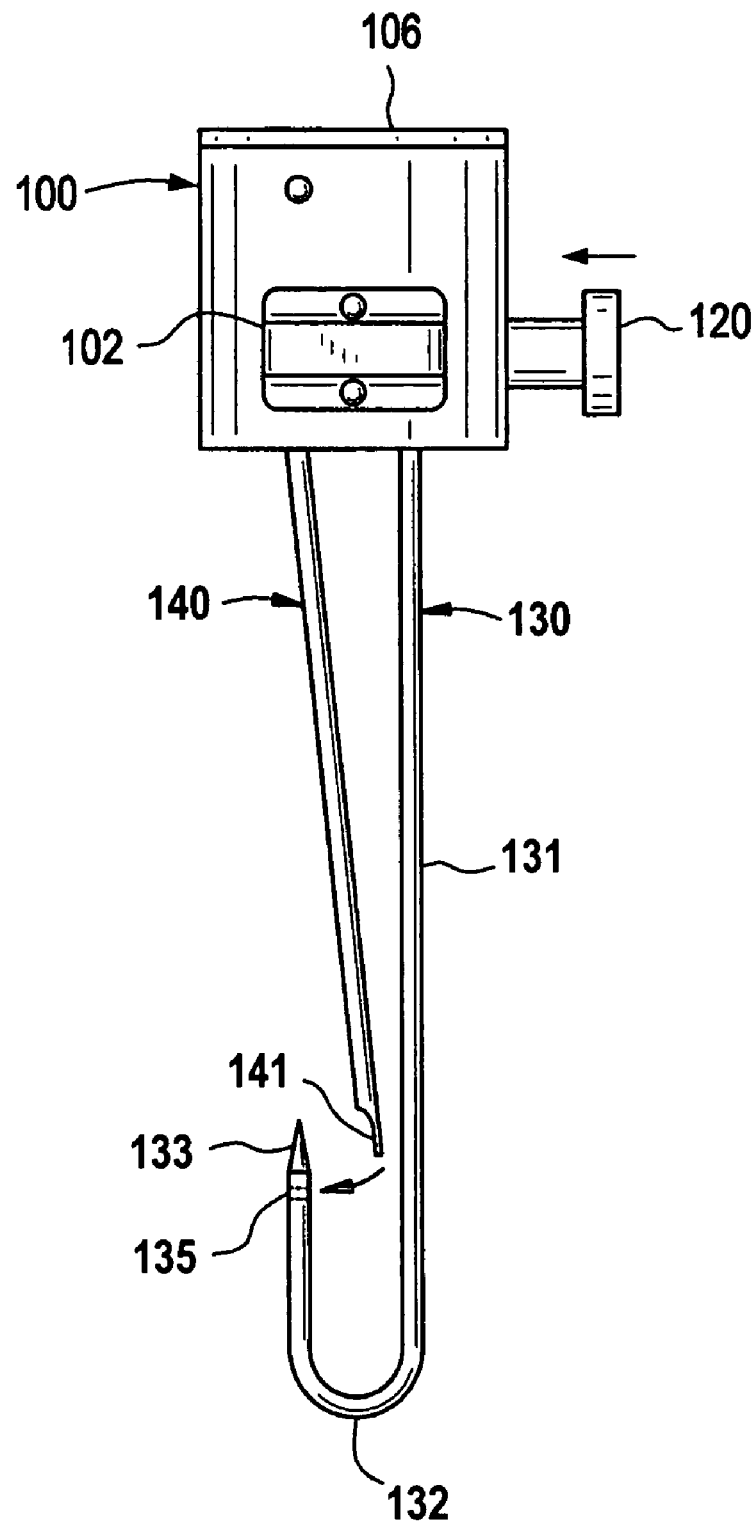
FIG. 2 shows an elevation view of a preferred embodiment of the present invention in the open position.

FIG. 2 shows an elevation view of the embodiment of FIG. 1 in the open position. When the thumb nut 120 is released, an internal compression mechanism (not shown) forces the thumb nut 120 out and the moveable arm 140 swings inward toward the needle shaft 131, exposing the needle tip 133. When the thumb nut 120 is depressed, the moveable arm 140 moves to the closed position, where the tip protector 141 at least partially covers the needle tip 133.

Figure 3:
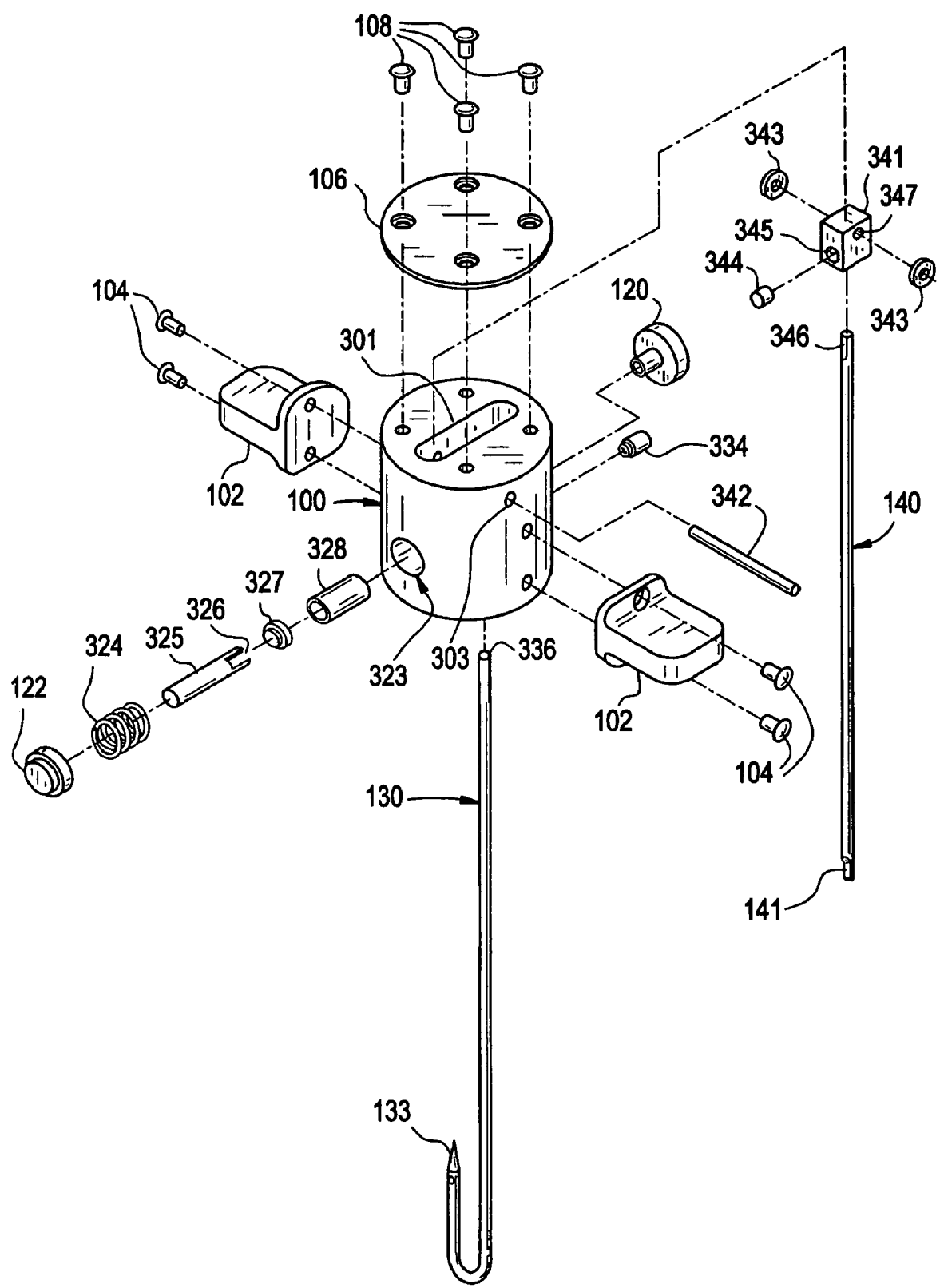
FIG. 3 shows an exploded view of a preferred embodiment of the present invention.

FIG. 3 shows an exploded view of a preferred embodiment of the present invention. FIG. 4 shows a cross-sectional view of the body 100. The upper end 336 of a needle 130 (shown in FIG. 3) is inserted into a hole 452 (shown in FIG. 4) that is drilled, cast, or otherwise formed into the underside of the body 100. The upper end 336 of the needle 130 may be retained in the hole 452 by friction or by a set screw 334 screwed into a tapped hole 454. The tapped hole 454 is drilled, cast or-otherwise formed into the body 100 and intersects with the hole 452, holding the upper end 336 of the needle 130.

A moveable arm chamber 301 is formed in the upper interior portion of the body 100. In a preferred embodiment, the moveable arm chamber 301 has at least two substantially parallel sides and is large enough to accommodate a moveable arm holder 341 and two washers 343. A dowel hole 303 is formed through the moveable arm chamber 301 normal to at least one side of the moveable arm chamber 301. An oblong or rectangular moveable arm hole 456 communicates between the bottom of the moveable arm chamber 301 and the bottom surface of the body 100.

A compression mechanism chamber 323 is drilled, cast, or otherwise formed through the body 100 below the moveable arm chamber 301. In a preferred embodiment, the compression mechanism chamber 323 is aligned with the long axis of the bottom of the moveable arm chamber 301. In a preferred embodiment, the compression mechanism chamber 323 has three concentric diameters, the largest portion 457 opening to one side of the body 100 and accepting a set screw 122, a medium diameter portion 458 disposed within the interior of the body 100 and accepting a plunger sleeve 328, and the smallest diameter portion 459 opening to the opposite side of the body 100 and accepting a thumb nut 120: The moveable arm hole 456 passes through and is approximately normal to the medium diameter portion 458. In alternate embodiments, the compression mechanism chamber 323 could comprise a hole of a single diameter, or have a non-circular cross-section.

A threaded plunger rod 325 with a moveable arm slot 326 is screwed to a captive nut 327 which is in turn screwed to a plunger sleeve 328. In alternate embodiments, these plunger components may be assembled with bayonet connectors, bonding, or other techniques well known in the art. The assembled plunger components are inserted into the interior of the compression mechanism chamber 323 and the moveable arm slot 326 is aligned so that a movable arm 140 may be passed upward through the moveable arm hole 456 and the moveable arm slot 326 into a hole (not shown) in the bottom of the moveable arm holder 341.

A set screw 344 is screwed into a tapped hole 345 formed in a side of the movable arm holder 341. The tapped hole 345 is normal to and intersects with the hole holding the movable arm 140. The set screw 344 presses against a flat surface 346 ground onto a side of the upper end of the movable arm 140, thereby adjustably locking the movable arm 140 within the movable arm holder 341.

With a washer 343 positioned on either side of a dowel hole 347, the assembled movable arm 140 and movable arm holder 341 are inserted into the movable arm chamber 301 with the moveable arm 140 passing through the movable arm hole 456 and the moveable arm slot 326, emerging from the bottom surface of the body 100. The dowel hole 347 in the movable arm holder 341 is aligned with the dowel hole 303 in the body 100. A dowel 342 is passed through the aligned dowel holes 303, 347 so that the movable arm 140 pivots on the dowel 342.

The dowel hole 303 in the body 100 is positioned so that the tip protector 141 mates properly with the needle tip 133. The movable arm 140 and the needle 130 may be shifted axially and rotated to effect a desired alignment.

The compression member 324 is inserted into the compression mechanism chamber 323 concentrically over the plunger rod 325. The set screw 122 is screwed in and tightened to hold the assembly in place. The thumb nut 120 is screwed into the plunger sleeve 328 from the opposite end of the compression mechanism chamber 323. The moveable arm chamber 301 is closed by a cover plate 106 held in place by screws 108. The handles 102 are attached to the body 100 with screws 104.

Figure 6A:
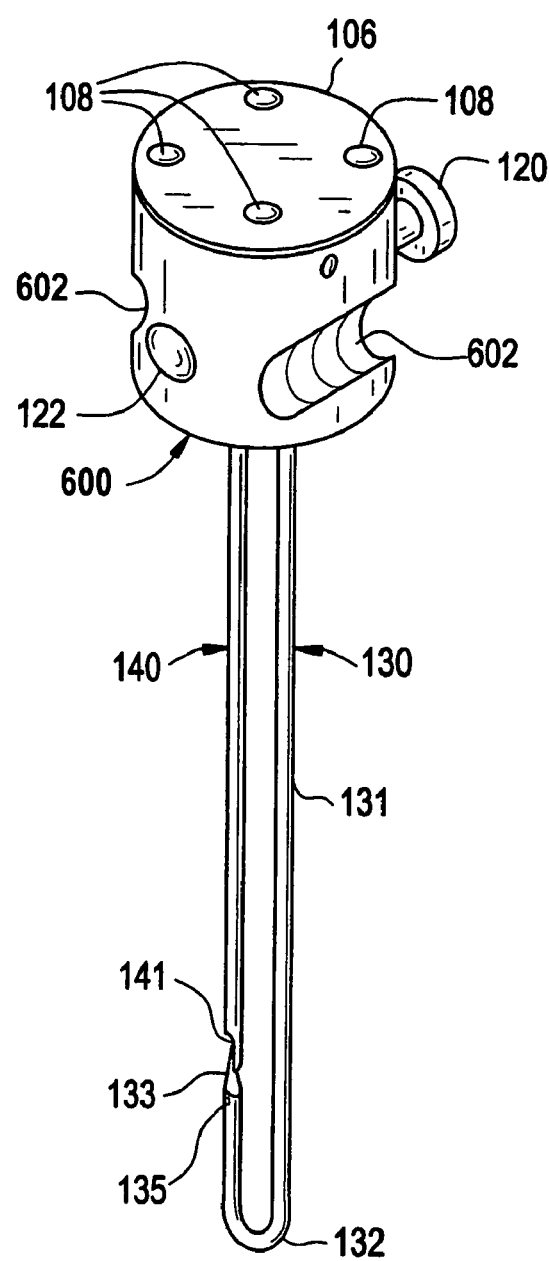
FIG. 6A shows a perspective view of an alternate embodiment of the present invention with finger depressions on opposite sides of the apparatus body.
Figure 6B:
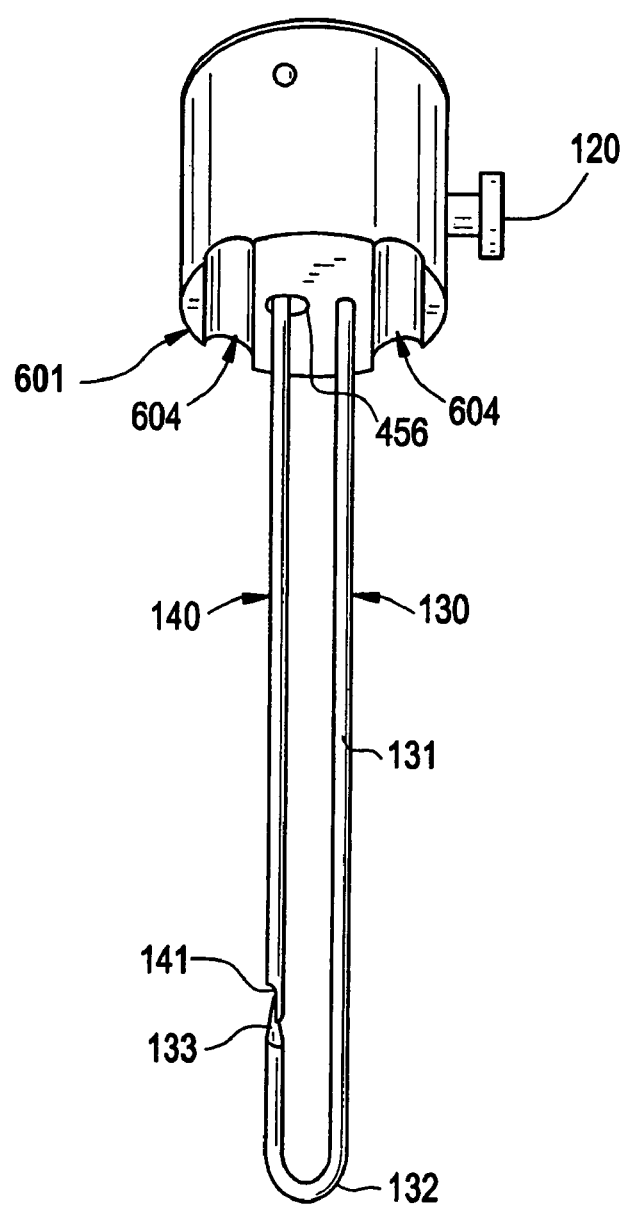
FIG. 6B shows a perspective view of an alternate embodiment of the present invention with finger depressions on the underside of the apparatus body.

In alternate embodiments, the handles 102 and the cover plate 106 may be attached by bonding agents, rivets, or other means known in the art. Alternatively, the handles 102 may be cast or otherwise formed as an integral part of the body 100. As shown in FIG. 6A, the handles may also be replaced by depressions 602 in the sides of the body 600. FIG. 6B shows an alternate embodiment in which the depressions 604 are positioned on the underside of the body 601. In each case, the depressions are sized, shaped, and positioned to accept a surgeon's fingers and provide a comfortable, secure grip on the apparatus. Apart from the use of depressions to provide gripping surfaces, the bodies 600, 601 shown in FIGS. 6A and 6B may comprise any of the materials, components, and configurations described elsewhere in this specification.

In a preferred embodiment, the compression member 324 (shown in FIG. 3) is a stainless steel compression spring, but other compression devices well-known in the art may serve the same purpose. In use, the compression member 324 reacts against the set screw 122 to urge the plunger rod 325, captive nut 327, plunger sleeve 328, and thumb nut 120 away from the set screw 122. Since the moveable arm 140 is captured in the moveable arm slot 326 and pivots on a dowel 342, the compression member 324 tends to force the moveable arm 140 to the open position. When the thumb nut 120 is depressed, the compression member 324 is compressed and the moveable arm 140 swings to the closed position, covering at least a portion of the needle tip 133 with the tip protector 141.

FIG. 5 shows a perspective view of a preferred needle tip design. The needle tip 133 in this embodiment is conical, but any shape useful for surgery may be employed. A hole 135 for suture material is bored radially through the needle a short distance below the base of the tip 133. In alternate embodiments, additional holes may be bored in any position and orientation desired by a surgeon.

A tip protector 141 is formed by grinding, milling, or otherwise forming a side of the lower end of the moveable arm 140 to approximately one-half of a full cross-section, leaving a curved or angled bevel 549 at the uppermost end of the tip protector 141. Further forming operations produce a receiving cavity 548 in the remaining portion of the tip protector 141. The receiving cavity 548 is sized and shaped to receive enough of the needle tip 133 to prevent the tip 133 from snagging tissue and to approximately align the full cross-sectional center of the tip 133 with the full cross-sectional center of the moveable arm 140. When the moveable arm 140 swings into the closed position, the aligned needle 130 may then be quickly inserted into and withdrawn from an incision without damage to tissue.

Utilizing the apparatus to expedite a common surgical technique, the surgeon holds the apparatus with the cover plate 106 against the palm of a hand and hooks a finger around each handle 102. Alternatively, when utilizing an embodiment equipped with finger depressions rather than handles, the surgeon holds the apparatus with the cover plate 106 against the palm of a hand and positions a finger within each depression. The surgeon inserts the needle 130 and moveable arm 140 into an incision. With the apparatus in a closed position, the surgeon manipulates the apparatus until the needle tip 133 is near the underside of the fascial layer at a location desirable for suture placement.

The surgeon releases the thumb nut 120, allowing the moveable arm 140 to swing to the open position. The apparatus is then pulled outward slightly, causing the needle tip 133 and hole 135 to pass through the tissue. The surgeon inserts a loop of suture material though the hole 135 below the needle tip 133. A free end of the suture material may be grasped with forceps, then the needle tip 133 is pushed back through the tissue. As the needle tip 133 emerges from the tissue, the surgeon presses the thumb nut 120, thereby covering the needle tip 133 with the tip protector 141.

The apparatus is then rotated so that the needle tip 133 is near a desired suture location on the opposite side of the incision. The surgeon releases the thumb nut 120 and passes the needle 130 far enough through tissue to allow the suture material to grasped with forceps. The suture material is cut and the apparatus is inserted into the body far enough to allow the needle tip 133 to be engaged by the tip protector 141. The thumb nut 120 is then pressed to return the apparatus to the closed position and the apparatus is quickly withdrawn from the incision, which is drawn and tied together with the remaining suture material. The surgeon may repeat this operation as many times as needed.

In another surgical technique, an embodiment with two holes 135 allows each end of a pre-cut length of suture material to be threaded into a different hole. The apparatus is lowered into an incision, the needle 130 is drawn through tissue, one suture end is removed, and the needle 130 is withdrawn and moved to a new location. The needle 130 is drawn through tissue again and the remaining end of the suture material is removed. The apparatus is closed and withdrawn from the incision and the suture is closed. Again, this procedure may be repeated as many times as necessary.

The principles, embodiments, and modes of operation of the present invention have been set forth in the foregoing specification. The embodiments disclosed herein should be interpreted as illustrating the present invention and not as restricting it. The foregoing disclosure is not intended to limit the range of equivalent structure available to a person of ordinary skill in the art in any way, but rather to expand the range of equivalent structures in ways not previously contemplated. Numerous variations and changes can be made to the foregoing illustrative embodiments without departing from the scope and spirit of the present invention.

The invention claimed is:

1. A suturing apparatus, comprising:
   a body;
   a J-shaped needle having a proximal end and a distal end, wherein
   the proximal end of the needle is attached to the body and comprises an elongated, straight portion of the J-shape, a first central axis is located within the proximal end of the needle,
   the distal end of the needle having comprising a tapered needle tip capable of penetrating tissue and having at least one passage to hold suture material, the tapered portion of the needle tip having a center line comprising the centroids of adjacent selected planer cross-sections of the tapered portion, each selected planar cross-section selected for having a smaller area than each proximally located planar cross-section having the same centroid as the selected planar cross-section, the distal end of the needle formed so that at least a first line is tangent to the center line and the first central axis portion;
a movable arm, the movable arm having a proximal end and a distal end,
the proximal end of the movable arm pivotally attached to the body,
the distal end of the movable arm consisting of a needle tip protector and pivoting from a closed position wherein the needle tip protector contacts the needle tip to an open position wherein the movable arm pivots toward the straight elongated portion of the J-shape and no longer contacts the needle tip; and
a movable part actuator, the movable part actuator operable to move the movable arm between the open position and the closed position.

2. A suturing apparatus as claimed in claim 1, wherein the movable arm actuator comprises a compression member, the compression member disposed within the body, the compression member operable to urge the movable arm to the open position.

3. A suturing apparatus as claimed in claim 2, wherein the compression member is a spring.

4. A suturing apparatus as claimed in claim 1, wherein the apparatus comprises materials capable of tolerating autoclave sterilization.

5. A suturing apparatus as claimed in claim 1, further comprising a first handle and a second handle, the first handle and the second handle attached to the opposite sides of the body.

6. A suturing apparatus as claimed in claim 1, further comprising a first depression and a second depression, the first depression and the second depression disposed upon opposite sides of the body in locations where they may accept an operator's fingers while the operator is placing the sutures.

7. A suturing apparatus as claimed in claim 1, further comprising a first depression and a second depression, the first depression and the second depression disposed upon the underside of the body in locations where they may accept an operator's fingers while the operator is placing the sutures.

8. A suturing apparatus as claimed in claim 1, wherein the apparatus is configured for left-handed use.

9. A suturing apparatus comprising:
a body;
a hook shaped needle, having a proximal end and a distal end, wherein
the proximal end of the needle is attached to the body and comprising an elongated, straight portion of the hook shape, a first central axis is located within the proximal end of the needle,
the distal end of the needle comprising a tapered needle tip capable of penetrating tissue and having at least one passage to hold suture material, the tapered portion of the needle tip having a center line comprising the centroids of adjacent selected planar cross-sections of the tapered portion, each selected planar cross-section selected for having a smaller area than each proximally located planar cross-section having the same centroid as the selected planar cross-section, the distal end of the needle formed so that at least a first line is tangent to the center line and the first central axis portion;
a movable arm, the movable arm having a proximal end and a distal end,
the proximal end of the movable arm pivotally within attached to the body,
the distal end of the movable arm consisting of a needle tip protector and pivoting from a closed position wherein the needle tip protector contacts the needle tip to an open position wherein the movable arm pivots toward the straight elongated portion of the hook-shape and no longer contacts the needle tip; and
a movable arm actuator the movable arm actuator operable to move the movable arm between the open position and the closed position and comprising a compression member disposed within the body,
the compression member operable to urge the movable arm to the open position.

10. A suturing apparatus as claimed in claim 9, wherein the apparatus comprises materials capable of tolerating autoclave sterilization.

11. A suturing apparatus as claimed in claim 9, wherein the apparatus is configured for left hand use.

12. A suturing apparatus as claimed in claim 9, further comprising a first handle and a second handle, the first handle and the second handle attached to opposite sides of the body.

13. A suturing apparatus as claimed in claim 9, further comprising a first depression and a second depression, the first depression and the second depression disposed upon opposite sides of the body.

14. A suturing apparatus as claimed in claim 9, further comprising a first depression and a second depression, the first depression and the second depression disposed upon the underside of the body.

* * * * *